(12) United States Patent
Darnell et al.

(10) Patent No.: US 9,265,869 B2
(45) Date of Patent: Feb. 23, 2016

(54) BREAST PUMP

(75) Inventors: Ian Philip Darnell, Cambridge (GB); Graham Trevor Cook, Harlow (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/003,006

(22) PCT Filed: Mar. 19, 2012

(86) PCT No.: PCT/IB2012/051305
§ 371 (c)(1),
(2), (4) Date: Sep. 4, 2013

(87) PCT Pub. No.: WO2012/127405
PCT Pub. Date: Sep. 27, 2012

(65) Prior Publication Data
US 2014/0052057 A1 Feb. 20, 2014

(30) Foreign Application Priority Data

Mar. 21, 2011 (EP) .................................... 11158958

(51) Int. Cl.
*A61M 1/06* (2006.01)
*A61J 13/00* (2006.01)
*A61M 1/00* (2006.01)

(52) U.S. Cl.
CPC . *A61M 1/06* (2013.01); *A61J 13/00* (2013.01); *A61M 1/066* (2014.02); *A61M 2001/0072* (2013.01); *A61M 2205/075* (2013.01)

(58) Field of Classification Search
CPC ............ A61M 1/06; A61M 2001/064; A61M 2001/066; A61M 2205/075; A61M 2001/0072; A61J 13/00
USPC ..................................................... 604/74, 75
See application file for complete search history.

(56) References Cited

U.S. PATENT DOCUMENTS

| 5,049,126 A | 9/1991 | Larsson | |
| 6,579,258 B1* | 6/2003 | Atkin | A61M 1/066 604/74 |
| 2003/0153869 A1* | 8/2003 | Ytteborg | A61M 1/066 604/74 |
| 2005/0154348 A1* | 7/2005 | Lantz | A61M 1/066 604/74 |
| 2005/0154349 A1* | 7/2005 | Renz | A61M 1/06 604/74 |
| 2005/0251089 A1 | 11/2005 | Lee et al. | |
| 2006/0148380 A1* | 7/2006 | Rousso | A41C 3/04 450/36 |
| 2008/0243061 A1* | 10/2008 | Britto | A61M 1/06 604/74 |
| 2008/0255503 A1* | 10/2008 | Quackenbush | A61M 1/0031 604/74 |
| 2009/0171270 A1* | 7/2009 | Rohrig | A61M 1/06 604/74 |
| 2010/0049122 A1* | 2/2010 | Jaeger-Waldau | A61M 1/06 604/74 |

FOREIGN PATENT DOCUMENTS

| DE | 19816776 A1 | 10/1999 |
| GB | 2340755 A | 3/2000 |
| WO | 2009006627 A2 | 1/2009 |

* cited by examiner

*Primary Examiner* — Emily Schmidt
*Assistant Examiner* — William Frehe (57) ABSTRACT

The present invention relates to a breast pump operable to generate a negative pressure comprising a funnel (24) for receiving a breast of a user. The breast pump (24) has an insert (50,70) receivable in the funnel (24) having a deformable region (59a-59e) which forms a chamber between the insert (50,70) and the funnel (24) when the insert (50,70) is received in the funnel (24). A passageway (37) connecting the chamber to the source of negative pressure is formed in the funnel (24) so that, during use, the deformable region (59a-59e) is deformed and/or deflected relative to the breast of a user in response to a negative pressure in the chamber.

10 Claims, 6 Drawing Sheets

BREAST PUMP

CROSS-REFERENCE TO PRIOR APPLICATIONS

This application is the U.S. National Phase application under 35 U.S.C. §371 of International Application No. PCT/IB2012/051305, filed on Mar. 19, 2012, which claims the benefit of EP 11158958.6, filed on Mar. 21, 2011. These applications are hereby incorporated by reference herein.

FIELD OF THE INVENTION

The present invention relates to a breast pump comprising a breast receiving funnel. The invention also relates to a breast pump or breast pump insert that provides an enhanced level of comfort for a user.

BACKGROUND OF THE INVENTION

Breast pumps are well known devices for extracting milk from a breast of a user. A breast pump may be used if the baby or infant is not itself able to express milk from the breast, or if the mother is separated from the baby or infant and is to be fed with breast milk by someone else. The use of a breast pump to express milk may also be used to stimulate and increase milk production in women with a low milk supply.

Breast pumps make use of a negative pressure to induce milk expression from a nursing mother's breast. The pumping action of the device draws the milk from the nipple to a collection vessel, and the pressure and/or frequency may generally be adjusted to the preferences of the user.

Figure 1:
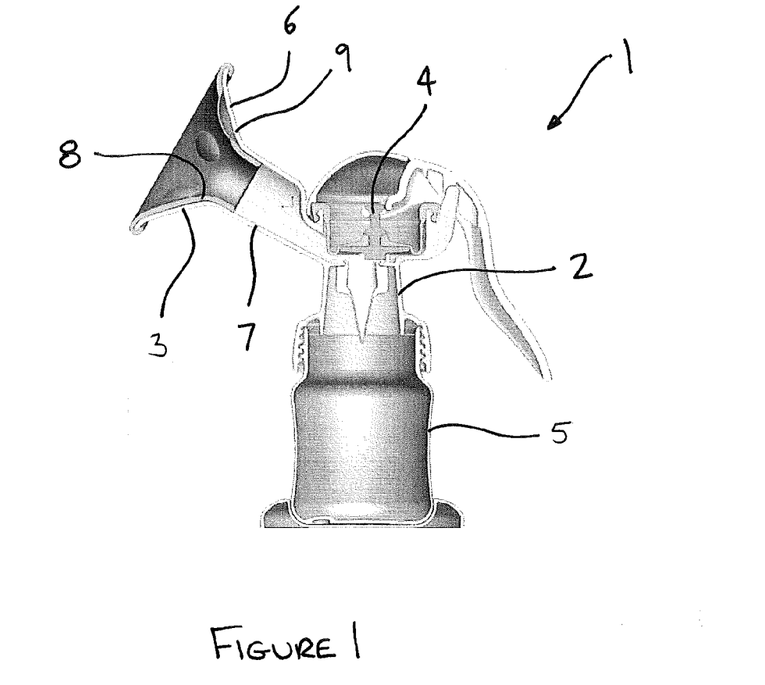
FIG. 1 shows a cross-sectional side view of an existing breast pump which is known from prior art.

A known breast pump for extracting milk from a user's breast is shown in FIG. 1. A breast pump 1 typically comprises a main body 2 with a rigid breast receiving funnel 3 connected to a vacuum pump unit 4 having a collection vessel 5 for collecting the milk, such as a feeding bottle or bag.

The breast-receiving funnel 3 extends from the main body 2 for receiving the breast of a user. The funnel 3 is generally frustoconically shaped and comprises a mouth 6 and a neck 7. The mouth 6 is open at an outer end and an inner surface 8 of an outer funnel wall 9 converges from the outer end towards the neck 7 to form a hollow cavity in which a user's breast is received.

A fluid path is defined by the mouth 6 and neck 7 of the funnel 3 and extending through the main body 2 to the collection vessel 5 so that milk expressed from a user's breast flows along the neck of the funnel 3, through the main body 2, and to the collection vessel 5.

Research has shown that when a baby is feeding at its mother's breast, it applies a peristaltic type of pressure to the mother's nipple sandwiched between its tongue and the roof of its mouth when it sucks on the nipple. This peristaltic pressure on the nipple draws milk from it. When the pressure is released, e.g. as the baby takes a breath or swallows, a new supply of milk flows into the nipple ready for a baby to extract it again once the "let down" reflex is activated due to the mother's "oxytocin" release.

Flexible resilient cushions or inserts are known which fit into the rigid funnel portion of a vacuum generating breast pump and have protrusions on them which massage the user's breast when a negative pressure is applied thereto. Such an insert is generally formed from a silicon or thermoplastic elastomer (TPE) in an attempt to improve a user's level of comfort and aid the expression of milk. An insert is described in the earlier filed European patent application 96301046.7.

Figure 2:
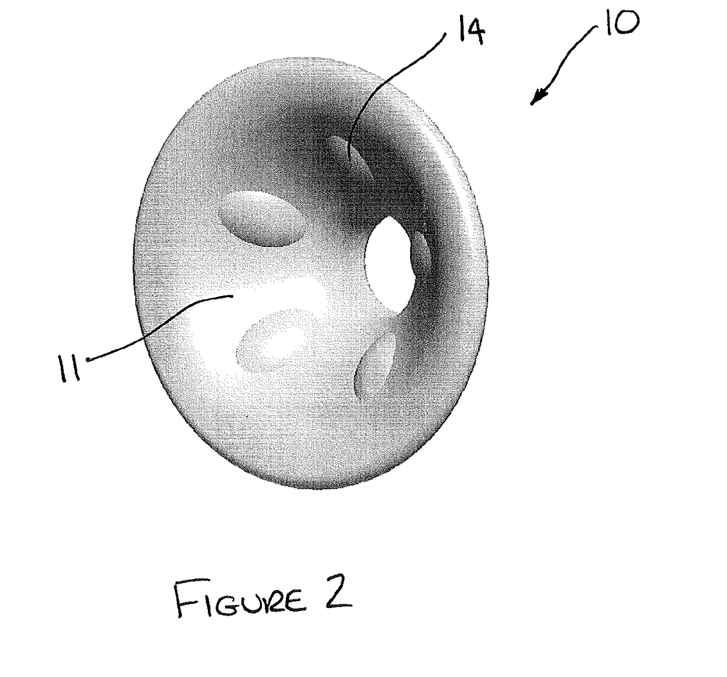
FIG. 2 shows a perspective view of an existing insert for the existing breast pump shown in FIG. 1 which is known from prior art.
Figure 3:
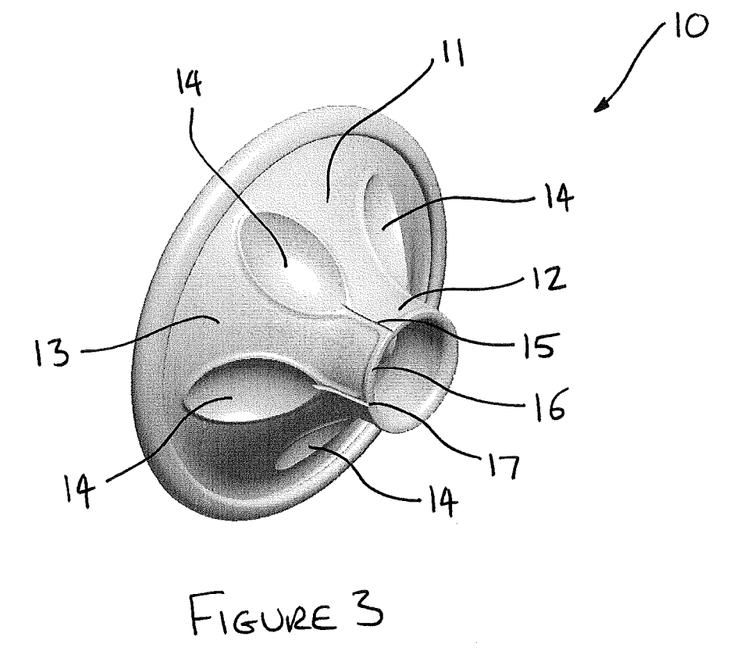
FIG. 3 shows another perspective view of the existing insert for the existing breast pump shown in FIG. 2 which is known from prior art.
Figure 4:
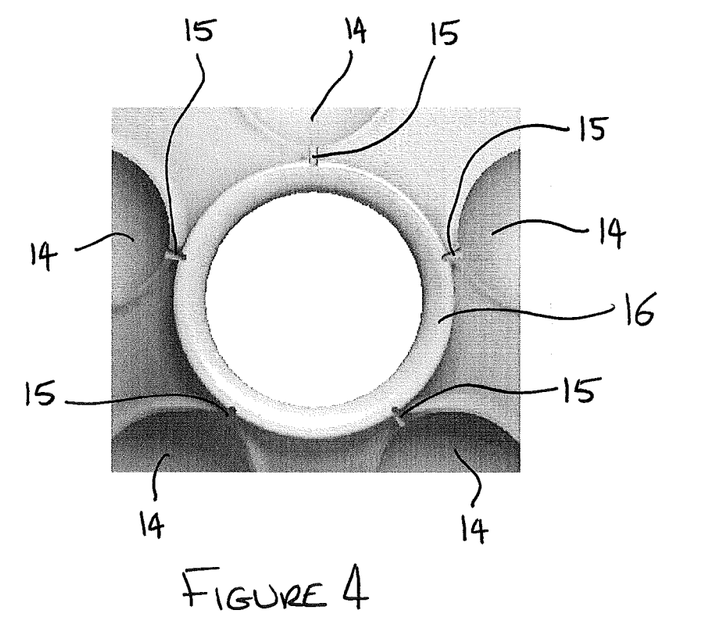
FIG. 4 shows a partial rear view of the existing insert shown in FIG. 2 which is known from prior art.

Such a known insert 10 is shown in FIGS. 2 to 4 prior to insertion into the rigid funnel portion of a known breast pump.

The flexible insert 10 includes a conical mouth portion 11 which is connected to a tubular inner portion 12. An outer surface 13 of the flexible insert 10 is configured to lie against the inner surface 8 of the rigid funnel wall 9 when the insert is disposed therein. The insert 10 has a plurality of axially spaced deformable recesses or pockets 14 formed in the outer surface 13 of the mouth portion 11, each recess 14 forming a vacuum chamber with the inner surface 8 of the funnel wall 9 when the insert is disposed therein. Each recess 14 has a channel 15 extending to a rear end 16 of the inner portion 12 to communicate each recess 14 with the tubular inner portion 12. Five recesses 14 are shown in FIGS. 2 to 4 arranged circumferentially around the mouth portion 11 and spaced from each other, each having a channel 15 extending therefrom to the rear end 16 of the inner portion 12, so that inlets 17 to the channels 15 are spaced circumferentially around the rear end 16. Therefore, when a user's breast is disposed in the funnel and locates against the inner surface of the insert and a negative pressure is cyclically formed by the vacuum pump unit 4, a negative pressure is formed in each recess 14 and the insert wall of the recess is caused to cyclically deform and deflect towards to the inner surface of the funnel wall causing them to move inwardly and outwardly relative to the user's breast in an attempt to massage the user's breast.

However, milk expressed from a user's breast into the funnel of the breast pump is known to pool in the funnel, against the insert, in particular when a user sits back in an attempt to relax and aid the user's "let down" reflex. Therefore, a problem with known breast pump arrangements is that milk pooling in the funnel lies against the insert and is able to flow along the channels communicating the recesses with the rear end of the insert, and is drawn into the channels due to the cyclical pressure generated. As a consequence, milk is known to flow between the insert and the inner surface of the rigid funnel wall and into the petals which will reduce their effectiveness at massaging a user's breast. Furthermore, milk can visibly collect between the rigid funnel wall and the insert, giving the impression to the user that there is a problem with the product or that it is leaking. In addition, milk may also leak out of the breast pump, between the funnel wall and the insert, and onto the user's breast or clothing causing discomfort to the user.

Expressed milk is considered to be very precious and is known to have a high emotional value to mothers that have expressed milk from their breasts. Therefore, this residual milk collecting between the funnel wall and the insert and leaking from the funnel is considered to be a loss to a user because the milk cannot be useably collected, and this loss of milk may have an emotional impact, such as a psychological loss, disappointment or distress, on the user.

SUMMARY OF THE INVENTION

Therefore, it is an object of the invention to provide a breast pump having a breast receiving funnel which substantially alleviates or overcomes at least one of the problems mentioned above.

It is known from DE19816776A1 to provide a breast pump operable to generate a negative pressure comprising a funnel for receiving a breast of a user, an insert receivable in the funnel having a deformable region which forms a chamber between the insert and the funnel when the insert is received in the funnel, and a cavity in which a negative pressure is generated by the source of negative pressure to draw milk through the cavity.

According to the present invention, there is provided a breast pump operable to generate negative pressure characterised in that an end of the insert seals against the funnel to separate the chamber from the cavity and a passageway is formed in the funnel to connect the chamber with the cavity so that, during use, the deformable region is deformed and/or deflected relative to the breast of a user in response to a negative pressure in the chamber.

The passageway may be formed at an upper end of the funnel so that, during use, the passageway is disposed above the nipple of a user.

The funnel having a passageway formed therein can help to restrict milk expressed from the user's breast from flowing between the insert and the funnel. Furthermore, an advantage of the above arrangement is that the passageway is spaced from any milk expressed from the user's breast that pools in the funnel.

The breast pump advantageously comprises a milk outlet configured to communicate with a milk receiving vessel, wherein the passageway is formed on a diametrically opposite side of the funnel to the milk outlet.

An advantage of this arrangement is that the passageway is spaced from the flow of breast milk expressed from the user's breast.

In one embodiment, the passageway is a channel formed in an inner surface of the funnel. Therefore, the passageway is easily formed during manufacture of the breast pump.

The insert may comprise a mouth portion which is shaped to receive a breast of a user, the channel being configured to extend beyond a remote end of the insert distal from the mouth portion when the insert is received in the funnel. Therefore, the channel advantageously communicates with a cavity defined by the funnel so that the chamber is connected to the source of negative pressure.

Conveniently, the inner surface of the funnel further comprises a circumferentially extending shoulder against which the remote end of the insert locates when the insert is received in the funnel, and the channel extends along the shoulder. An advantage of this arrangement is that the insert can locate and seal against the insert, and the channel is open to the cavity defined by the funnel so that the chamber is connected to the source of negative pressure.

Preferably, the insert comprises two or more deformable regions which are spaced from each other and each form a chamber between the insert and the funnel when the insert is received in the funnel. Therefore, the ability of the insert to massage the user's breast is improved.

Advantageously, the passageway is a first passageway and the breast pump further comprises a second passageway configured to connect the two or more chambers to each other when the insert is disposed in the funnel. Therefore, the first passageway is simply connected to each of the two or more chambers.

Conveniently, the first passageway is configured to communicate with the second passageway and/or one of the chambers when the insert is received in the funnel.

Advantageously, the second passageway is configured to be disposed between each chamber and the remote end of the insert, and each chamber has a third passageway to connect said chamber to the second passageway.

An advantage of the aforementioned arrangements is that the first passageway communicates with the second passageway irrespective of the orientation of the insert in the funnel.

In one embodiment, the second passageway is a channel in the insert. Therefore, the second passageway is easily formed together with the chambers.

Advantageously, a continuous upstanding bead extends along each side of the second passageway and around each recess which is configured to form a fluid tight seal with the inner surface of the funnel when the insert is received in the funnel. Therefore, a fluid tight seal about each recess and along the length of the second passageway.

In another embodiment, the second passageway is an annular channel in the funnel. An advantage of the above arrangement is that the second passageway is formed together with the first passageway and so is always in communication with the first passageway.

The breast pump may comprise a circumferentially extending rib upstanding from the remote end of the insert which is configured to seal against the inner surface of the funnel to form a fluid tight seal with the inner surface of the funnel when the insert is received in the funnel.

The breast pump may further comprise another circumferentially extending rib upstanding from the remote end of the insert which is spaced from and extends parallel to the circumferentially extending rib which is configured to seal against the inner surface of the funnel to form a fluid tight seal with the inner surface of the funnel when the insert is received in the funnel.

Therefore, the insert is sealed against the inner surface of the funnel and so milk is prevented from flowing therebetween.

BRIEF DESCRIPTION OF THE DRAWINGS

Preferred embodiments of the invention will now be described, by way of example only, with reference to the accompanying drawings, in which.

DETAILED DESCRIPTION OF THE EMBODIMENTS

Figure 5:
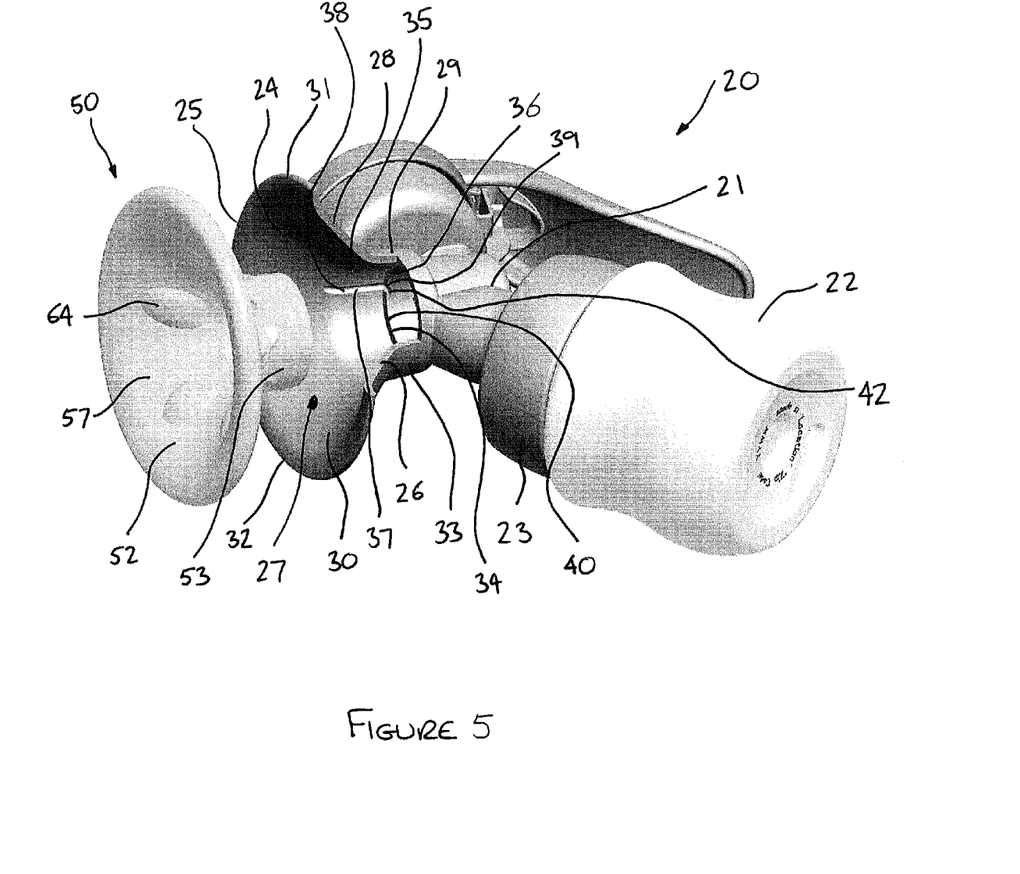
FIG. 5 shows an exploded perspective view of a breast pump with an insert, with a partial cut-away of a breast receiving funnel of the breast pump.
Figure 6:
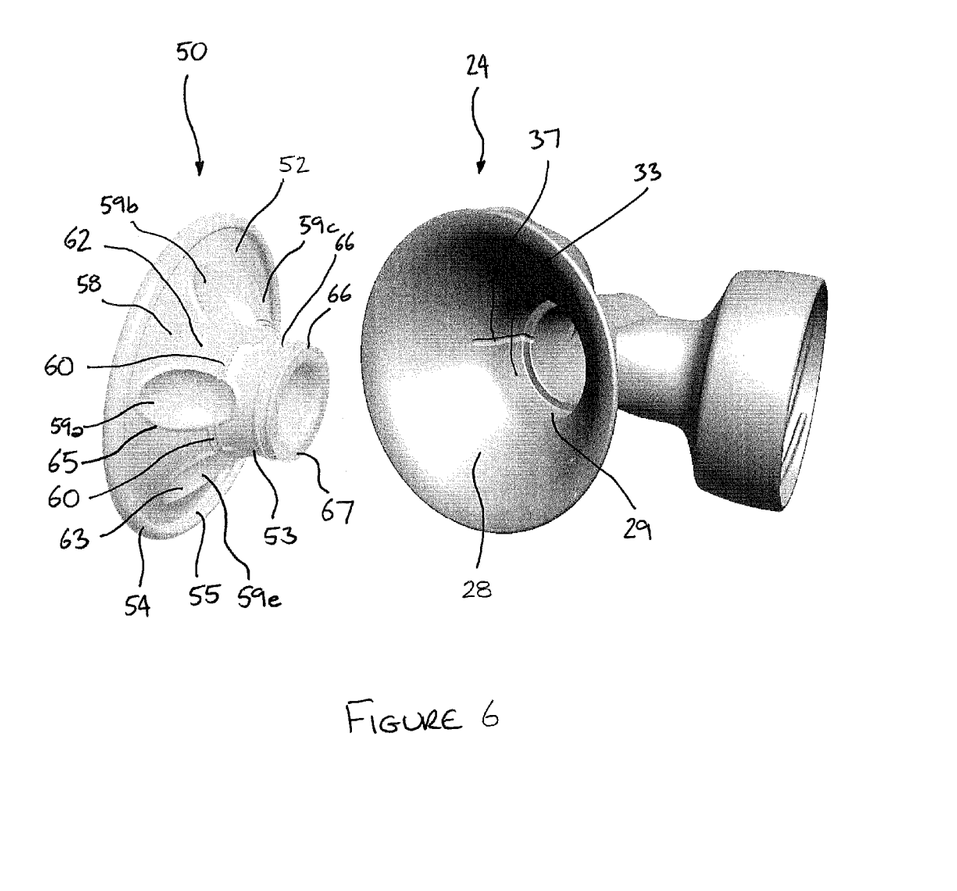
FIG. 6 shows an exploded perspective view of a body of the breast pump with the breast receiving funnel and the insert shown in FIG. 5.
Figure 7:
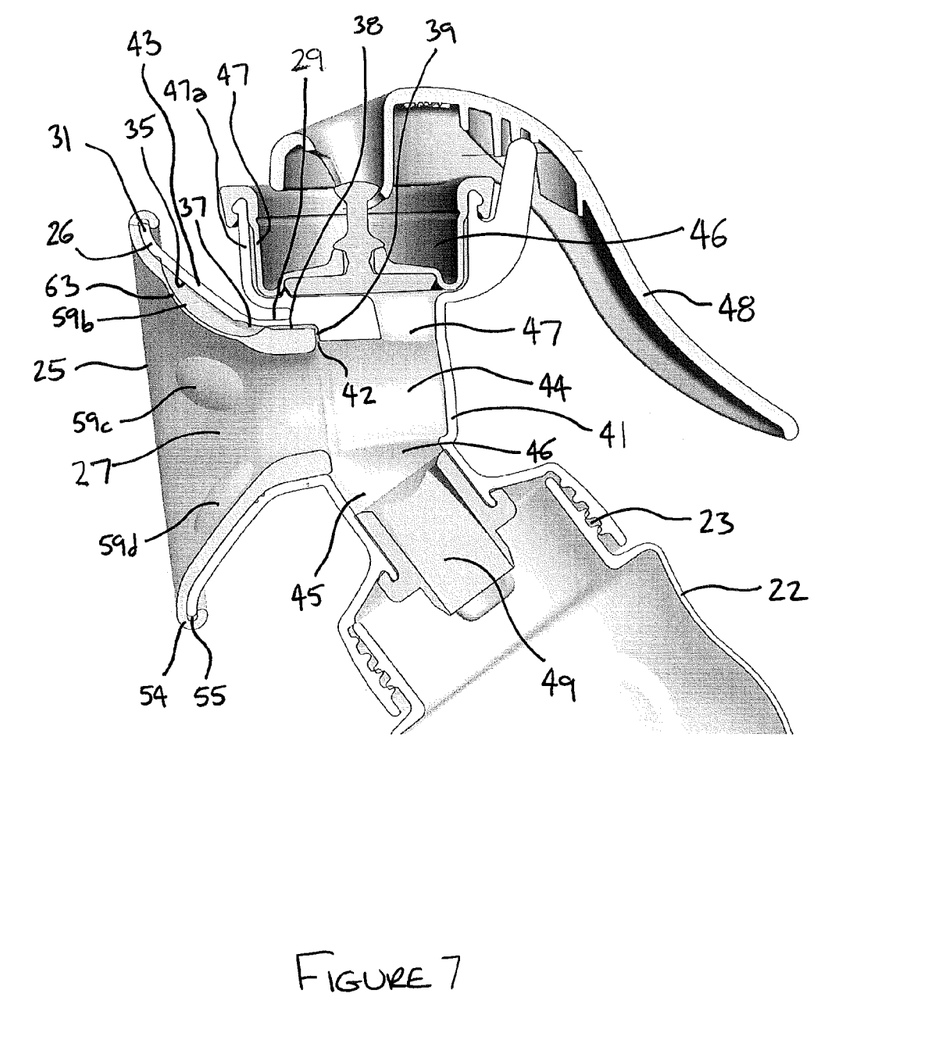
FIG. 7 shows a cross-sectional view of the breast pump shown in FIG. 5.

Referring now to FIGS. 5 to 7, a breast pump 20 is shown. The breast pump 20 comprises a main body 21 and a feeding bottle 22 for an infant or baby, acting as a milk-receiving vessel. The milk receiving vessel 22 is attached to the main body by a screw fitting 23, although it will be understood that alternative releasable attachment means may be used, such as clips (not shown).

A breast receiving funnel 24 extends from the main body 21 of the breast pump 20. The funnel 24 comprises an opening 25, through which a user inserts their breast, and an outer wall 26 which defines a hollow funnel cavity 27. The outer wall 26 extends from the main body 21 and is integrally formed therewith.

The breast receiving funnel 24 comprises a mouth section 28 and a neck section 29. The mouth 28 has a generally frustoconical shaped wall 30 which converges from the opening 25 to the funnel 24 at an outer end 32, towards the neck 29. The neck 29 has a tubular wall 33, and extends between the mouth 28 and the main body 21. The mouth 28 has an outwardly extending flange 31 around its circumference at the opening 25, for reasons that will become apparent hereinafter.

The frustoconical wall 30 of the mouth 28 and the tubular wall 33 of the neck 29 together form the funnel outer wall 26, and they are integrally formed with each other and main body 21. The funnel 24 and the main body 21 are formed from a rigid, non-deformable material, such as a rigid plastic, for ease of manufacture and to allow sterilisation, although alternative suitable materials may be used.

Although in the present embodiment the funnel 24 is integrally formed with the main body 21 of the breast pump, it will be understood that in an alternative embodiment the funnel 24 is removably mounted thereto. Such a funnel 24 is removably mounted to the main body 21 of the breast pump to aid cleaning or sterilisation of the funnel 24 and main body 21.

A shoulder 34 extends circumferentially around, and upstands in, an inner surface 35 of the outer wall 26. A circumferentially extending face 36 of the shoulder 34 faces the opening 25 to the funnel 24. In the present embodiment the shoulder 34 is formed in the tubular wall 33 of the neck 29, although it will be appreciated that the shoulder 34 may be formed in the frustoconical wall 30 of the mouth 28.

A duct, conduit or channel 37 is disposed in the outer wall 26 extending in the direction of the longitudinal axis of the funnel 24. The channel 37 is an elongate recess formed in the inner surface 35 of the funnel outer wall 26 and extends along the tubular wall 33 of the neck and partially along the frustoconical wall 30 of the mouth 28. A first section 38 of the channel 37 extends from the funnel mouth 28 to the face 36 of the shoulder 34 and a second section 39 of the channel 37 extends from the first channel section 38 to an inner edge 40 of the shoulder 34, to form a channel inlet 42. The channel 37 is formed in an upper end 43 of the funnel 24 such that, when the breast pump is orientated in its correct operating position (as shown in FIG. 7), the channel 37 is disposed at the uppermost part of the funnel 24, above a user's nipple. It will be appreciated that the upper end 43 of the funnel 24 is the upper side of the mouth 28 and neck 29 when the breast pump is disposed in its correct operating orientation, with the feeding bottle lowermost.

The main body 21 comprises an outer shell 41 and has a main chamber or cavity 44 formed therein. A milk outlet 45 extends downwardly from a lower side 46 of the main chamber 44. The milk receiving vessel 22 is attached to the main body 21 at a lower end of the milk outlet 45. Therefore, the neck 29 of the funnel 24 fluidly communicates with the main chamber 44, and the main chamber 44 fluidly communicates with the milk receiving vessel 22 through the milk outlet 45 so that milk expressed from the user's nipple flows into the milk receiving vessel 22 during operation of the breast pump, as will become apparent hereinafter.

A vacuum pump unit 46 is mounted to, and fluidly communicates with, an upper side 47 of the main body 21 which is used to cyclically create a vacuum in the main chamber 44, and therefore the funnel cavity 27. The vacuum pump unit 46 comprises a resilient, deformable diaphragm 47 disposed in a diaphragm chamber 47a. The diaphragm 47 is resiliently deformed when operated by means of a user manually operating a handle 48 which acts on the diaphragm 47, or by means of an electric motor (not shown) to cyclically create a negative pressure in the main chamber 44 and in the funnel cavity 27, when a user's breast is disposed in the mouth section 28 of the funnel 24. A one way valve 49 is disposed between the main chamber 44 and the collection vessel 22 to prevent a vacuum being created in the collection vessel 22, but to allow milk to flow into the collection vessel 22.

A flexible, resilient insert 50 is shown in FIGS. 5 and 6 just prior to insertion into the funnel 24. The insert 50 is moulded in one piece and includes a conical mouth portion 52 which is connected to a tubular inner portion 53 whose outer diameter is slightly smaller than the internal diameter of the tubular wall 33 of the neck 29. The outer edge of the mouth portion 52 is moulded with an annular rim 54 which includes a rebate 55 therein (refer to FIG. 7) so that the insert 50 can be attached to the outwardly extending flange 31 on the funnel mouth 28 to make a fluidtight seal therewith. A user's breast locates against an inner surface 57 of the insert 50 when the insert is disposed in the funnel 24.

The insert 50 has an outer surface 58, and recesses or pockets 59a-59e are formed in the outer surface 58 at the mouth portion 52. The recesses 59a-59e are, for example, oval or petal, as illustrated, and extend partially along the insert inner portion 53, although it will be appreciated that the recesses 59a-59e may be formed in the insert mouth portion 52 only. A circumferentially extending duct, conduit or channel 60 is moulded in the outer surface 58 of the insert mouth portion 52 and extends between each recess 59a-59e, so that a portion of the conduit 60 extends from one recess to an adjacent one, for reasons that will be explained hereinafter. Each recess 59a-59e forms a pressure chamber defined between the inner surface 35 of the outer funnel wall 26 and the base wall 63 of each recess when the insert 50 is received in the funnel cavity 27.

Five recesses 59a-59e are shown in the illustrated embodiment which are arranged circumferentially around the flexible mouth portion 52 and spaced apart by equal amounts to leave thicker fingers 62 therebetween. It will be appreciated that the thickness of the mouth portion in the region of the finger portions 62 is the full thickness of the mouth portion wall whereas in the region of the recesses 59a-59e, the base wall 63 of each recess 59a-59e is of a reduced thickness (in particular, refer to FIG. 7). Therefore, it will be appreciated that during use of the breast pump, a base wall 63 of the recess regions 59 forms a deformable region which is able to deform to act on the breast of a user.

Although five recesses are illustrated, it will be appreciated that the number and configuration of the recesses is not critical. For instance, an annular pocket may be formed. The base wall 63 of each recess 59a-59e is arcuate so that the inner surface 57 of the insert in the region of the recesses 59a-59e protrudes inwardly and upstands from the remainder of the inner surface 57 to form protrusions 64. This helps to improve the stimulation effect of the insert 50.

An upstanding bead 65 extends alongside the circumferentially extending conduit 60 and around each recess 59a-59e. In use, this bead 65 is deflected into contact with the inner surface 35 of the outer funnel wall 26 to form a fluid tight seal therewith when the insert 50 is disposed in the funnel 24. Therefore, each portion of the circumferentially extending conduit 60 forms a passageway between adjacent recesses defined by the walls of the channel portions and the inner surface 35 of the outer funnel wall 26. In the above embodiment the circumferentially extending conduit 60 is formed by the upstanding bead 65, although it will be appreciated that in another embodiment the conduit may be formed by a line cut into the outer surface 58 of the insert 50.

Two circumferentially extending sealing ribs 66 extend around the tubular inner portion 53 at a remote end 67 of the insert 50 from the conical mouth portion 52. The two sealing ribs 66 are spaced from each other and extend parallel to each other. An advantage of the above arrangement is that a fluid tight seal is provided between the insert 50 and the funnel 24 at the remote end 67 of the insert 50, with the exception of the single passageway formed by the channel 37 in the upper end 43 of the funnel 24. Although two sealing ribs 66 are shown, it will be appreciated that in an alternative embodiment there is a single sealing rib or more than two sealing ribs. Alternatively, the remote end 67 of the insert forms an interference fit with the funnel outer wall 26.

In use, the flexible insert 50 is received in the funnel 24 and is attached to the outer wall 26 by engaging the annular rim 54 over the outwardly extending flange 31 of the funnel mouth 28 to form a fluidtight seal therewith. The tubular inner portion 53 of the flexible insert 50 extends into the neck section 29 of the funnel 24 and the two sealing ribs 66 at the remote end 67 of the insert 50 locate against the inner surface 35 of the outer funnel wall 26 to form a fluid tight seal therewith. Furthermore, the remote end 67 of the insert 50 abuts against the shoulder 34. It will be appreciated that a passageway is formed by the channel 37 in the inner surface 38 of the funnel 24 which bypasses the sealing ribs 66 to connect the pressure chambers defined by the recesses 59a-59e with the funnel cavity 27. Although in the embodiment described herein, a shoulder 34 is formed in the inner surface 35 of the funnel 24, it will be appreciated that in an alternative embodiment that no shoulder is present and the channel 37 extends further along the inner surface 35 of the funnel 24 than the remote end 67 of the insert 50.

When the insert 50 is properly attached to the funnel 24, it is located as shown in FIG. 7. The passageway formed by the channel 37 in the funnel inner surface 35 is open to the funnel cavity 27, and the upstanding bead 65 extending alongside the circumferentially extending conduit 60 and around each recess 59a-59e locates against the inner surface 35 of the funnel 24 to form a fluid tight seal therewith. It will be appreciated that the channel 37 in the funnel 24 extends along the inner surface 35 of the funnel 24 to intersect with either the circumferentially extending conduit 60 formed in the insert outer surface 58 or one of the recesses 59a-59e so that each of the recesses 59a-59e is fluidly connected with the inside of the funnel 24. An advantage of the above arrangement is that only a single channel is required to extend from the remote end 67 of the insert 50 to connect the funnel cavity 27 with all of the recesses 59a-59e. Furthermore, the channel 37 in the funnel 24 intersects with the circumferential conduit 60 in the insert 50, or the recesses 59a-59e themselves, so that the recesses 59a-59e fluidly connect with the channel 37 in the funnel 24 irrespective of the orientation of the insert 50 in the funnel 24.

When a user inserts their breast through the opening 25 into the funnel cavity 27, it will be appreciated that the breast fills the mouth section 28 and seals against the inner surface 57 of the insert 50 to form a fluid seal. When a negative pressure is generated by the vacuum pump unit 46 in a known manner a negative pressure is formed in the funnel cavity 27. The channel 37 in the funnel wall 26 forms a passageway so that the recesses 59a-59e are fluidly connected to the funnel cavity 27. Therefore, a negative pressure is formed in the recesses 59a-59e when a negative pressure is generated by the vacuum pump unit 46. The recesses communicating with the source of negative pressure causes the base wall 63 of each recess 59a-59e, which is of a reduced thickness, to collapse and be sucked outwardly into contact with the inner surface 35 of the funnel 24. On release of the negative pressure, the recesses 59a-59e return to their original configuration and thereby apply a pressure on the user's breast to massage the user's breast and/or stimulate the nipple. As the vacuum pump unit 46 cyclically generates a negative pressure, the process is repeated on a cyclic basis to stimulate milk flow form the user's breast when disposed in the breast receiving funnel 24.

As milk is expressed from the user's breast it flows, and may pool, in a lower side of the funnel 24. However, milk is prevented from flowing between the inner surface 35 of the funnel 24 and the outer surface 58 of the insert 50 by the ribs 66 at the remote end 67 of the insert 50 locating against the inner surface 35 of the outer funnel wall 26 to form a fluid tight seal therewith. Furthermore, during use, the breast pump is correctly orientated by the user, with the milk outlet 45 extending downwardly from a lower side 46 of the main chamber 44, so that milk flows into the feeding bottle 22. As the channel 37 in the funnel wall 26 is formed in the upper side of the funnel wall 26, on a diametrically opposite side of the funnel to the milk outlet 45, milk cannot flow into the channel 37 in the funnel wall 26. This means that milk expressed from a user's breast does not flow along the passageway formed by the channel 37 and into the recesses 59a-59e formed between the funnel inner surface 35 and the insert outer surface 58.

An advantage of the channel 37 which forms the passageway between the funnel cavity 27 and the recesses 59a-59e being formed in the funnel outer wall is that the channel 37 is disposed in the upper part of the funnel independent of the orientation of the insert 50 in the funnel 24.

Although in the above described embodiment the upstanding bead 65 extending alongside the circumferentially extending conduit 60 and around each recess 59a-59e locates against the inner surface 35 of the outer funnel wall 26 to form a fluid tight seal therewith, it will be appreciated that in another embodiment the outer surface 58 of the insert 50 locates directly against the funnel inner surface 35 to form a fluid tight seal therewith. In such an embodiment, the upstanding two sealing ribs 66 at the remote end 67 of the insert 50 may be omitted.

Figure 8:
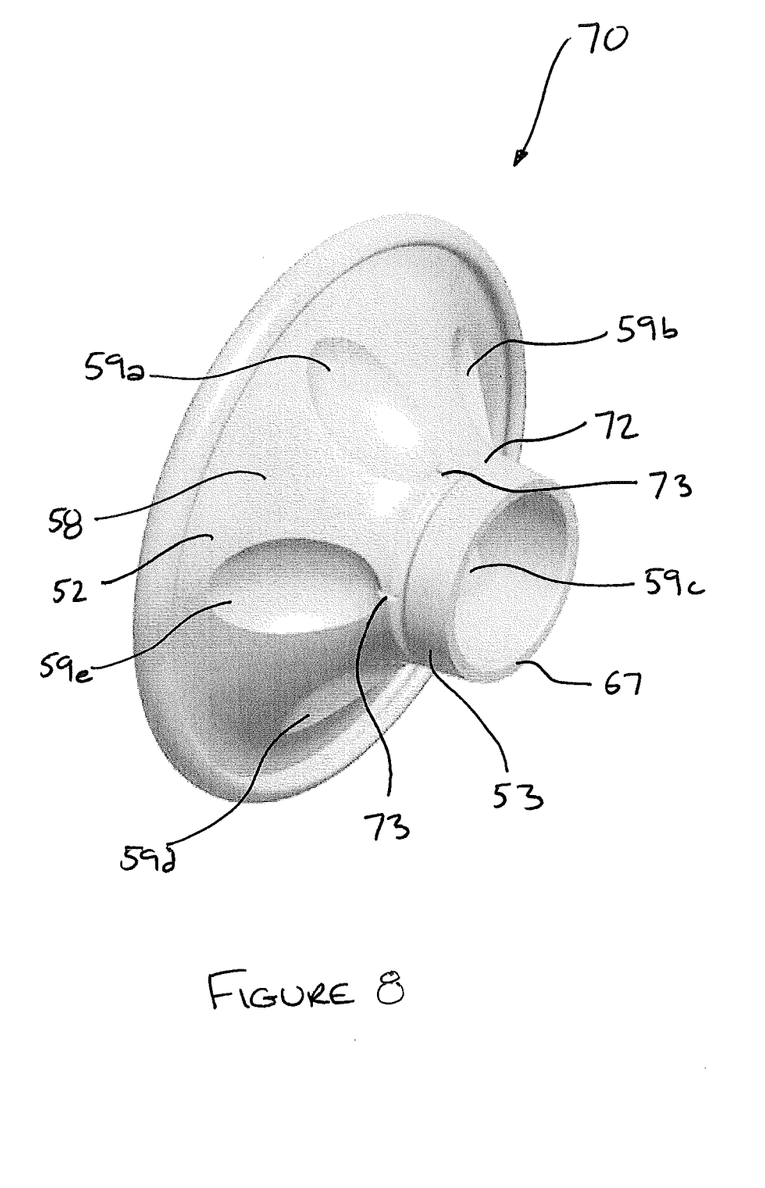
FIG. 8 is a perspective view of an alternative insert for the breast pump shown in FIG. 5.

For example, referring to FIG. 8 an alternative insert 70 for use in the funnel described above will now be described. The insert 70 is generally the same as the insert described above, and so a detailed description will be omitted herein. Furthermore, components and features corresponding to features and components described in the foregoing embodiment will retain the same reference numerals.

In this embodiment, a circumferentially extending conduit 72 is formed in the outer surface 58 of the insert 70. The conduit 72 is disposed between the recesses 59a-59e and the remote end 67 of the insert 70 from the conical mouth portion 52. The conduit 72 is formed by a circumferentially extending trough formed in the outer surface 58, and each recess 59a-59e has a conduit, duct or channel 73 connecting each recess 59a-59e to the circumferentially extending conduit 72. The duct 73 extends in a direction of the longitudinal axis of the insert and defines a fluid passageway between each recess and the circumferentially extending conduit 72.

During use, the insert 70 is received in the funnel 24 and is attached therein as described above. It will be appreciated that the outer diameter of the tubular inner portion 53 is equal to or slightly larger than the internal diameter of the internal diameter of the tubular wall 33 of the neck section 29 respectively so that the outer surface 58 of the insert 70 locates against and forms a fluid tight seal with the inner surface 35 of the outer funnel wall 26, with the exception of the single passageway formed by the channel 37 in the upper end 43 of the funnel 24.

It will be appreciated that the seal is formed via an interference fit of the tubular inner portion 53 of the insert 70 in the neck 29 of the funnel 24.

The channel 37 in the funnel wall 26 extends along the funnel wall 26 to intersect with the circumferentially extending conduit 72 and extends beyond the remote end 67 of the insert 70 when the insert 70 is received in the funnel 24. Therefore, the channel 37 is in fluid communication with each of the recesses 59a-59e independent of the orientation of the insert 70 in the funnel 24.

Although in the above described embodiments the circumferentially extending conduit which communicates each of the recesses with each other is formed in the insert, it will be appreciated that in an alternative embodiment the circumferentially extending conduit is formed in the inner surface of the funnel. In such an embodiment, the conduit extends circumferentially around the inner surface of the funnel and the channel forms an open junction therewith in the funnel.

In connection with the second aspect of the invention referred to above, it will be appreciated that one or both of the inserts of the first aspect of the invention may be provided with a textured surface. The present invention also includes within its scope a single breast pump insert having a textured breast interface contact surface, as well as a funnel for a breast pump having such a surface.

The textured surface may cover all or part of the funnel or insert. For example, there can be a series of repeated patterns extending around the circumference of the insert or cushion each of which have a surface texture. In one preferred embodiment, there is a ring of smooth or untextured surface extending around the circumference of the insert or funnel to ensure that a proper seal is formed with a breast inserted therein. The smooth region can be at the mouth of the insert or funnel, i.e. at the end or outer border where the breast is inserted or, it can be spaced inwardly so as to divide the textured surface into two regions separated by said ring.

If an insert is provided with a series of petals, as previously mentioned above, the surface texture could be associated with those petals, i.e. the surface texture may only be on the surface of the insert forming the petals. Alternatively, it could surround the petals.

The textured surface may be formed from a surface having a metric arithmetical mean roughness (Ra) in the order of single digits to tens of digits that reduces the overall surface contact between the user's skin and the breast pump. However, more preferably the metric arithmetical mean roughness is between 1 and 50 Ra or even 1 to 3 Ra.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claims in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump comprising:
    a funnel for receiving a breast of a user,
    an insert receivable in the funnel and having a plurality of deformable regions spaced from each other, each of said plurality of deformable regions forming a chamber between the insert and the funnel when the insert is received in the funnel, wherein said deformable regions are deformed relative to the breast of the user in response to a negative pressure in the chamber,
    a cavity in which said negative pressure is generated by a source of negative pressure to draw milk through the cavity wherein an end of the insert seals against the funnel to separate the chamber from the cavity; and
    a channel in and at an upper end of the funnel to connect all of the chambers with the cavity, wherein the channel is disposed above a nipple of the user, and wherein the channel is formed inside a wall of the funnel.

2. The breast pump according to claim 1, wherein the channel is a first passageway and the breast pump further comprises:
    a second passageway configured to connect the chambers formed by each of the plurality of deformable regions to each other when the insert is disposed in the funnel.

3. The breast pump according to claim 2, wherein the first passageway is configured to communicate with at least one of the second passageway and one of the chambers when the insert is received in the funnel.

4. The breast pump according to claim 3, wherein the second passageway is configured to be disposed between each chamber and the end of the insert, and each chamber has a third passageway to connect said chamber to the second passageway.

5. The breast pump according to claim 4, wherein the second passageway is a channel in the insert.

6. The breast pump according to claim 4, wherein the second passageway is an annular channel in the funnel.

7. The breast pump according to claim 1, wherein the insert comprises:
    a mouth portion shaped to receive said breast and the channel being configured to extend beyond an end of the insert distal from a mouth portion when the insert is received in the funnel.

8. The breast pump according to claim 7, wherein an annular rim of the mouth portion of the insert sealably attaches to an outer end of the funnel.

9. The breast pump according to claim 1 further comprising:
    a milk outlet configured to communicate with a milk receiving vessel, wherein the channel is formed on a diametrically opposite side of the funnel to the milk outlet.

10. The breast pump according to claim 1, further comprising:
    a circumferentially extending rib upstanding from the end of the insert configured to seal against the inner surface of the funnel to form a fluid tight seal with the inner surface when the insert is received in the funnel.

* * * * *